(12) United States Patent
Nakanishi

(10) Patent No.: US 8,731,267 B2
(45) Date of Patent: May 20, 2014

(54) X-RAY COMPUTED TOMOGRAPHY APPARATUS AND IMAGE PROCESSING APPARATUS

(75) Inventor: Satoru Nakanishi, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 223 days.

(21) Appl. No.: 12/892,091

(22) Filed: Sep. 28, 2010

(65) Prior Publication Data

US 2011/0075907 A1  Mar. 31, 2011

(30) Foreign Application Priority Data

Sep. 30, 2009 (JP) ................................. 2009-228575
Aug. 24, 2010 (JP) ................................. 2010-187532

(51) Int. Cl.
 *G06K 9/00* (2006.01)
(52) U.S. Cl.
 USPC .......................................................... 382/131
(58) Field of Classification Search
 None
 See application file for complete search history.

(56) References Cited

U.S. PATENT DOCUMENTS

| 2008/0187195 | A1* | 8/2008 | Kohler et al. ................. | 382/128 |
| 2009/0028288 | A1* | 1/2009 | Horiuchi et al. ................. | 378/4 |
| 2009/0110139 | A1* | 4/2009 | Noshi et al. ................. | 378/4 |
| 2010/0111393 | A1* | 5/2010 | Okumura et al. ............. | 382/131 |
| 2010/0121183 | A1* | 5/2010 | Taguchi et al. ............... | 600/427 |
| 2011/0105884 | A1* | 5/2011 | Beck ............................ | 600/410 |
| 2011/0142314 | A1* | 6/2011 | Hsieh et al. .................... | 382/131 |
| 2011/0142315 | A1* | 6/2011 | Hsieh et al. .................... | 382/131 |
| 2011/0150305 | A1* | 6/2011 | Zeng et al. .................... | 382/131 |
| 2011/0243404 | A1* | 10/2011 | Li .................................. | 382/128 |
| 2012/0141007 | A1* | 6/2012 | Takizawa et al. ............. | 382/131 |
| 2013/0170609 | A1* | 7/2013 | Nett et al. ......................... | 378/4 |
| 2013/0182932 | A1* | 7/2013 | Chen et al. .................... | 382/131 |

FOREIGN PATENT DOCUMENTS

| JP | 2002-325758 | 11/2002 |
| JP | 2007-159958 | 6/2007 |
| JP | 2009-045449 | 3/2009 |

OTHER PUBLICATIONS

Japanese Office Action mailed Mar. 11, 2014, in Japanese Patent Application No. 2010-187532 (with English-language translation).

* cited by examiner

*Primary Examiner* — John Strege
*Assistant Examiner* — Sean Conner
(74) *Attorney, Agent, or Firm* — Oblon, Spivak, McClelland, Maier & Neustadt, L.L.P.

(57) ABSTRACT

According to one embodiment, An X-ray CT apparatus includes acquisition unit, intermediate image generating unit, weighting factor calculating unit, and resultant image generating unit. The intermediate image generating unit generates a first image based on a first projection data set and a second image based on a second projection data set. The first projection data set falls within a first view angle range of projection data acquired by the acquisition unit. The second projection data set falls within a second view angle range of the projection data. The second view angle range is narrower than the first view angle range. The weighting factor calculating unit calculates a weighting factor corresponding to a pixel value difference between the first image and the second image. The resultant image generating unit generates a resultant image associated with weighted addition of the first image and the second image based on the weighting factor.

21 Claims, 4 Drawing Sheets

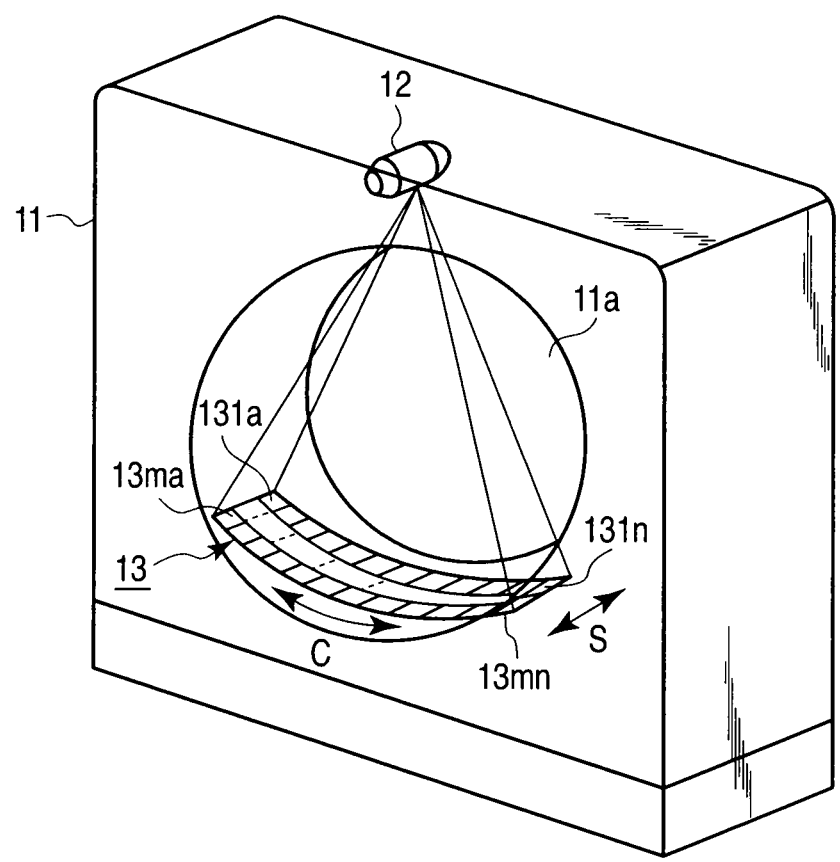
F I G. 2

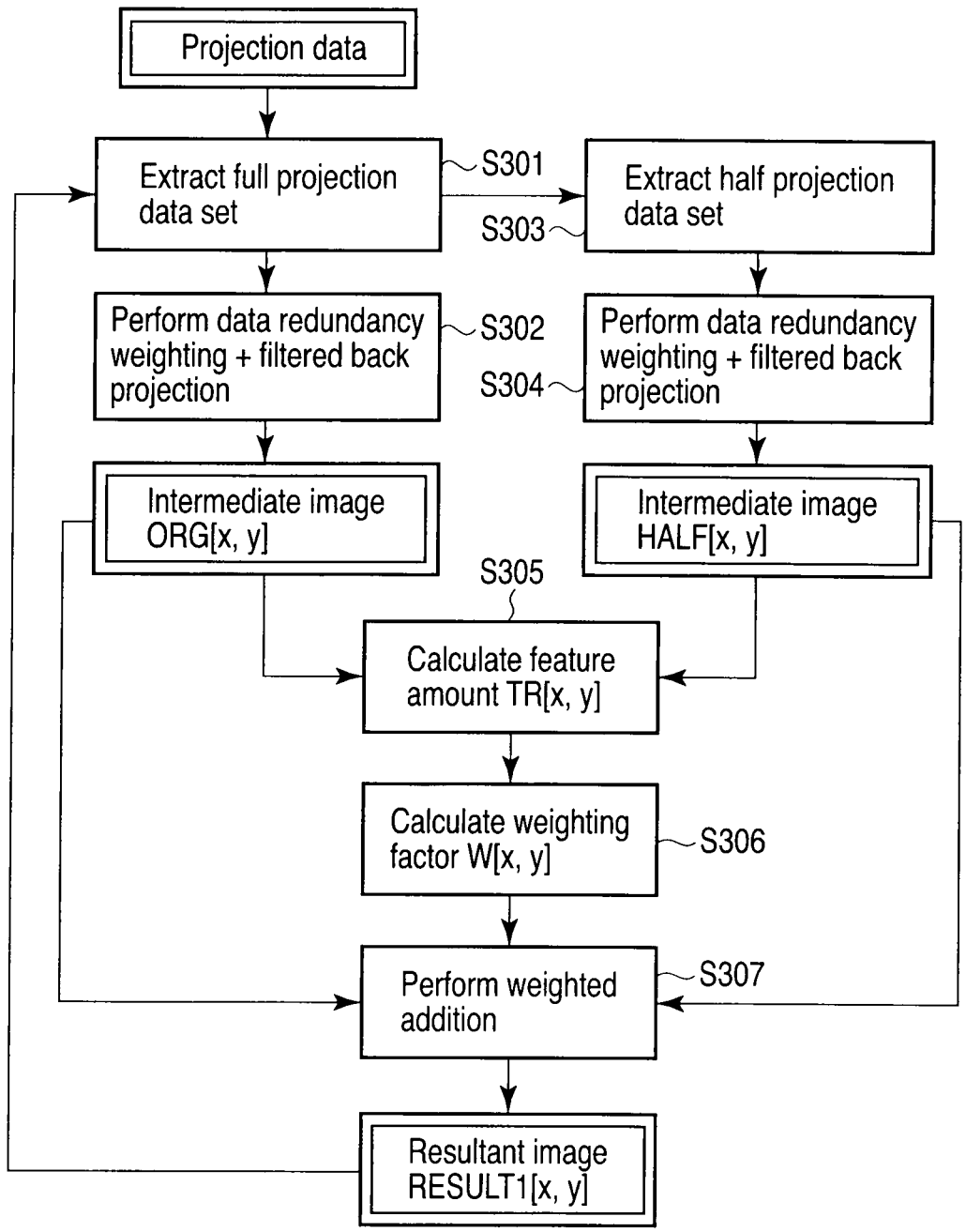
F I G. 3

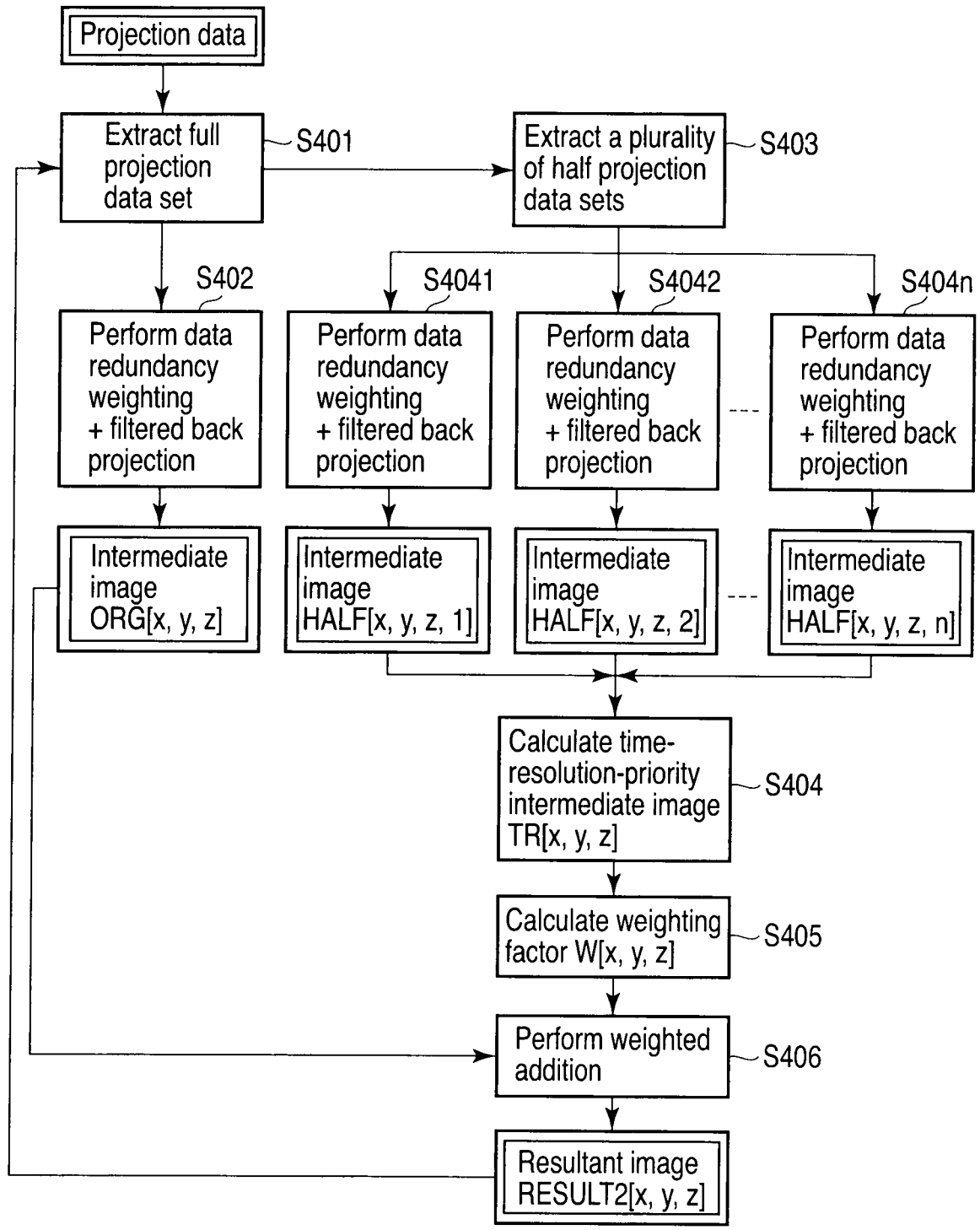
F I G. 4

US 8,731,267 B2

X-RAY COMPUTED TOMOGRAPHY APPARATUS AND IMAGE PROCESSING APPARATUS

CROSS-REFERENCE TO RELATED APPLICATIONS

This application is based upon and claims the benefit of priority from Japanese Patent Applications No. 2009-228575, filed Sep. 30, 2009; and No. 2010-187532, filed Aug. 24, 2010; the entire contents of both of which are incorporated herein by reference.

FIELD

Embodiments described herein relate generally to an X-ray computed tomography apparatus and an image processing apparatus.

BACKGROUND

The scanning schemes used by X-ray computed tomography apparatuses (X-ray CT apparatuses) are roughly classified into circular orbit scanning and helical scanning. The bed is not moved during circular orbit scanning. The bed is moved along the body axis of a subject during helical scanning.

A multi-array X-ray detector including a large number of X-ray detector arrays, e.g., 64 arrays, has recently been introduced. Introducing multi-array X-ray detectors has increased the occasion of scanning a wide range from a chest region to an abdominal region of a subject with one helical scan. In this case, in order to reduce image noise, the beam pitch is set to 1 or less, which is relatively slow.

In some cases, the lung fields are helically scanned with X-rays. The lungs are located near the heart, and always move accompanying the pulsation of the heart. When the beam pitch is set to 1 or less in helical scanning of the lung fields, projection data which can contribute to image reconstruction is acquired by an amount corresponding to one or more rotations of the X-ray tube. Using all these projection data for image reconstruction will generate high-quality image data with reduced image noise. In contrast to this, when projection data corresponding to one or more rotations is used for image reconstruction, the movement of the lungs accompanying heartbeats sometimes degrades the time resolution and makes the image less sharp.

BRIEF DESCRIPTION OF THE DRAWINGS

FIG. 2 is a schematic view of the structure of a gantry in FIG. 1;

FIG. 3 is a flowchart showing a typical procedure for the operation of an X-ray CT apparatus according to the first embodiment; and FIG. 4 is a flowchart showing a typical procedure for the operation of an X-ray CT apparatus according to the second embodiment.

DETAILED DESCRIPTION

Figure 1:
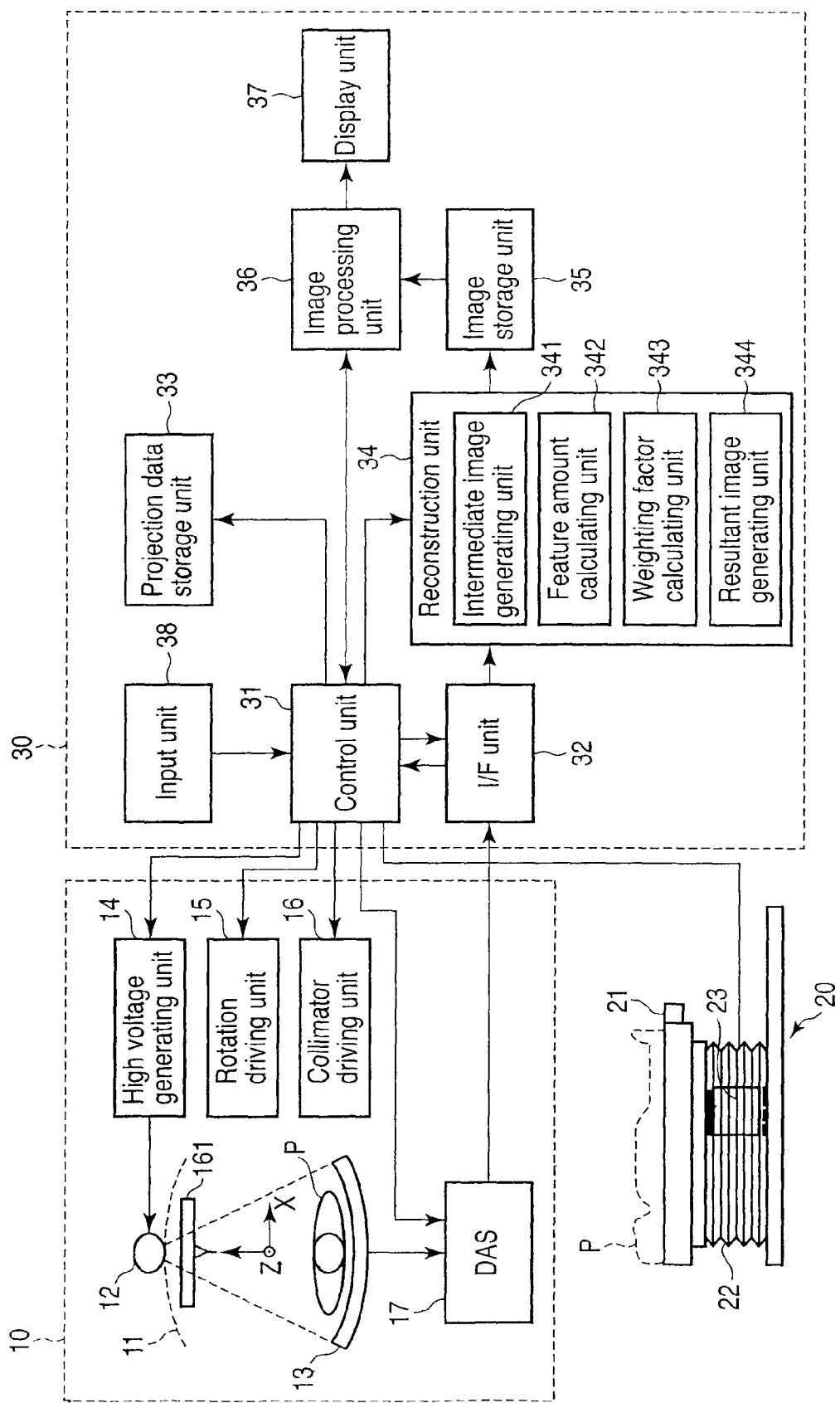
FIG. 1 is a block diagram showing the schematic arrangement of an X-ray CT apparatus according to this embodiment.

In general, according to one embodiment, an X-ray CT apparatus includes an X-ray tube, X-ray detector, support mechanism, control unit, acquisition unit, intermediate image generating unit, weighting factor calculating unit, and resultant image generating unit. The X-ray tube generates X-rays. The X-ray detector detects the X-rays which are generated by the X-ray tube and transmitted through a subject. The support mechanism rotatably supports the X-ray tube and the X-ray detector. The control unit controls the support mechanism to rotate the X-ray and the X-ray detector. The acquisition unit acquires projection data associated with the subject via the X-ray detector. The intermediate image generating unit generates a first intermediate image based on a first projection data set. The first projection data set falls within a first view angle range of the projection data. The intermediate image generating unit generates a second intermediate image based on a second projection data set. The second projection data set falls within a second view angle range of the projection data. The second view angle range is narrower than the first view angle range. The weighting factor calculating unit calculates a weighting factor corresponding to a pixel value difference between the first intermediate image and the second intermediate image. The resultant image generating unit generates a resultant image associated with weighted addition of the first intermediate image and the second intermediate image based on the weighting factor.

An X-ray CT apparatus and image processing apparatus according to this embodiment will be described below with reference to the views of the accompanying drawing.

First Embodiment

FIG. 1 is a block diagram showing the arrangement of an X-ray CT apparatus according to this embodiment.

As shown in FIG. 1, the X-ray CT apparatus includes a gantry 10, a bed 20, and an image processing apparatus 30. The gantry 10 includes a rotating frame 11. The rotating frame 11 includes an X-ray tube 12 and an X-ray detector 13. The X-ray tube 12 and the X-ray detector 13 are mounted on the rotating frame 11 so as to face each other through a subject P. The gantry 10 includes a high voltage generating unit 14, a rotation driving unit 15, a collimator driving unit 16, and a DAS 17.

The rotating frame 11 supports the X-ray tube 12 and the X-ray detector 13 so as to allow them to rotate about the rotation axis. The rotation axis intersects with the midpoint of a straight line connecting the X-ray focus of the X-ray tube 12 to the center of the detection surface of the X-ray detector 13, and is perpendicular to the straight line. The rotating frame 11 rotates about the rotation axis upon receiving the driving signal supplied from the rotation driving unit 15. The rotation driving unit 15 rotates the rotating frame 11 in accordance with a control signal from a control unit 31. The control unit 31 will be described later.

In this case, an XYZ orthogonal coordinate system is introduced. The Z-axis is defined by the rotation axis of the rotating frame 11. The Y-axis is defined by an axis connecting the X-ray focus of the X-ray tube 12 to the center of the detection surface of the X-ray detector 13. The Y-axis is perpendicular to the Z-axis. The X-axis is defined by an axis perpendicular to the Y- and Z-axes. In this manner, the XYZ orthogonal coordinate system forms a rotating coordinate system which rotates together with the rotation of the X-ray tube 12.

The high voltage generating unit 14 applies a high voltage corresponding to a scan condition to the X-ray tube 12 in accordance with a control signal from the control unit 31. Upon receiving the high voltage from the high voltage generating unit 14, the X-ray tube 12 generates X-rays. An X-ray shield plate (collimator) is movably provided near the X-ray window provided for the X-ray tube 12. X-rays are shaped into a fan shape or cone shape in accordance with the shape of the aperture of the collimator. The collimator driving unit 16 moves the collimator in accordance with a scan condition to adjust the irradiation range in the slice direction of X-rays.

The X-ray detector 13 detects the X-rays which are generated by the X-ray tube 12 and transmitted through the subject P, and outputs an electrical signal corresponding to the intensity of the detected X-rays. As shown in FIG. 2, the X-ray detector 13 includes a plurality of X-ray detection elements 131$a$ to 13 nm which are one- or two-dimensionally arranged. N (e.g., 1,000) X-ray detection elements are arranged along an arc (the inner surface of an opening portion 11$a$ of the rotating frame 11) centered on the Z-axis. The arrangement direction of the X-ray detection elements is called a channel direction C. The plurality of X-ray detection elements 131$a$ to 13 nm arranged along the channel direction C are called X-ray detector arrays. Only m arrays (e.g., 64 arrays) of the plurality of X-ray detector arrays are arranged along a slice direction S parallel to the Z-axis.

As shown in FIG. 1, the DAS (Data Acquisition System) 17 is connected to the X-ray detector 13. The DAS 17 acquires electrical signals corresponding to the intensities of X-rays detected by the X-ray detection elements. The DAS 17 amplifies the acquired electrical signals and converts them into digital signals. An electrical signal converted into a digital signal is called projection data. In other words, the DAS 17 acquires projection data associated with the subject P via the X-ray detector 13.

The bed 20 includes a top 21 on which the subject P is placed. A base 22 supports the top 21 to allow it to move along the Z-axis. The base 22 includes a top driving unit 23. The top driving unit 23 calculates the moving amount of the top 21 per rotation of the rotating frame 11 based on the control signal output from the control unit 31. The top driving unit 23 moves the top 21 along the Z-axis (parallel to the body axis of the subject P) in accordance with the calculated moving amount at the time of helical scanning.

The image processing apparatus 30 includes the control unit 31. The high voltage generating unit 14, rotation driving unit 15, collimator driving unit 16, DAS 17, and top driving unit 23 described above are connected to the control unit 31.

In addition to the control unit 31, the image processing apparatus 30 includes an I/F (interface) unit 32, a projection data storage unit 33, a reconstruction unit 34, an image storage unit 35, an image processing unit 36, a display unit 37, and an input unit 38.

The control unit 31 functions as the nerve center of the X-ray CT apparatus. For example, the control unit 31 supplies a control signal to the high voltage generating unit 14 to control the generation of X-rays. The control unit 31 supplies a control signal to the rotation driving unit 15 to control the rotation of the rotating frame 11. The control unit 31 supplies a control signal to the DAS 17 to control the acquisition of projection data. The control unit 31 supplies a control signal to the collimator driving unit 16 to control the aperture of the collimator. In addition, the control unit 31 supplies a control signal to the top driving unit 23 to control the movement of the top 21.

The I/F unit 32 receives projection data from the DAS 17. The projection data storage unit 33 stores the projection data input via the I/F unit 32. The reconstruction unit 34 reconstructs an image associated with the subject P based on the projection data. The reconstruction unit 34 will be described later. The image storage unit 35 stores the data of the reconstructed image. The image processing unit 36 performs various types of image processing for a reconstructed image to generate a CT image to be displayed. The display unit 37 displays the CT image. The input unit 38 is used to set various kinds of scan conditions and reconstruction conditions and input various kinds of instructions for failure diagnosis.

The reconstruction unit 34 includes an intermediate image generating unit 341, a feature amount calculating unit 342, a weighting factor calculating unit 343, and a resultant image generating unit 344. These constituent elements will be described below.

In this case, a set of projection data used for the reconstruction of one image will be referred to as a projection data set. A set of projection data acquired by one X-ray irradiation will be referred to as a view. A view angle corresponds to the rotation angle of the X-ray tube 12 about the rotation axis Z. A view angle range is defined by an angle range from a given view angle to another view angle. A view angle range includes a plurality of views. The width of a view angle range corresponds to the number of views, i.e., the amount of projection data.

The intermediate image generating unit 341 generates the first intermediate image based on a projection data set, of the projection data acquired by the DAS 17, which is associated with the first view angle range. The intermediate image generating unit 341 generates the second intermediate image based on a projection data set, of the projection data acquired by the DAS 17, which is associated with the second view angle range. The second view angle range is narrower than the first view angle range. In other words, the number of views included in the second view angle range is smaller than the number of views included in the first view angle range. The upper limit of the first view angle range is defined by the number of views which can contribute to the image reconstruction of a reconstruction slice at a given slice position (z position). The number of views is determined in accordance with scan conditions such as a beam pitch and a helical pitch and reconstruction conditions such as a reconstruction algorithm. Note that a beam pitch is defined by (helical pitch/number of X-ray detector arrays). The lower limit of the second view angle range is defined by the number of views corresponding to 180°+fan angle. That is, letting A be the number of views as the upper limit, B be the number of views as the lower limit (corresponding to 180°+fan angle), a be the number of views in the first view angle range, and b be the number of views in the second view angle range, the limitation defined by (A≥a)>(b≥B) is provided. In this case, a projection data set including all the views which can contribute to the image reconstruction of a reconstruction slice will be referred to as a full projection data set. In addition, a projection data set, of a full projection data set, which includes the number of views corresponding to 180°+fan angle will be referred to as a half projection data set.

For example, the intermediate image generating unit 341 reconstructs an intermediate image ORG based on a full projection data set, and reconstructs an intermediate image HALF based on a half projection data set. The intermediate image ORG is handled as the first intermediate image, and the intermediate image HALF is handled as the second intermediate image.

If, for example, the beam pitch is 0.5, and the number of views of a full projection data set corresponds to two rotations (i.e., 720°), the intermediate image generating unit 341 applies weighting for data redundancy correction to a full projection data set, and generates a weighted full projection data set. The intermediate image generating unit 341 then generates the intermediate image ORG from the weighted full projection data set by using a filter+three-dimensional back projection method typified by the Feldkamp method. Data redundancy correction in this case includes a weight which is set in accordance with view directions to equalize the respective numbers of views.

The weight to be used in this embodiment is not limited to this. Basically, any value can be used as the weight to be used in the embodiment as long as redundancy correction is properly performed for all the projection data corresponding to two rotations. In addition, although the case of using the three-dimensional back projection method has been described, the embodiment is not limited to this. For example, it is possible to use helical interpolation which was used in the early period of the advent of multislices.

In the case of the intermediate image HALF, the intermediate image generating unit 341 extracts a half projection data set (projection data corresponding to 180°+fan angle) from a full projection data set. For example, the center of the half projection data set in the view direction coincides with the view position of the reconstruction slice. The intermediate image generating unit 341 then applies weighting for data redundancy correction to the extracted half projection data set in the same manner as described above to generate a weighted half projection data set. The intermediate image generating unit 341 then generates the intermediate image HALF from the weighted half projection data set by using the filter+three-dimensional back projection method. As weighting for data redundancy correction in this case, for example, the weighting proposed by Parker is used. Note that it is possible to use the above helical interpolation instead of the weighting proposed by Parker.

The feature amount calculating unit 342 calculates a feature amount corresponding to the pixel value difference between the first intermediate image and the second intermediate image for each pixel. More specifically, the feature amount calculating unit 342 calculates feature amounts concerning the respective pixels of the first and second intermediate images which have the same coordinates. A feature amount is typically the absolute value of the difference between pixel values. For example, the feature amount calculating unit 342 calculates the absolute values of the differences between the respective pixels of the intermediate image ORG and the intermediate image HALF which have the same coordinates. However, this embodiment is not limited to this. Other feature amounts include, for example, a correlation coefficient obtained by pattern matching and the vector length of an optical flow.

The weighting factor calculating unit 343 calculates a weighting factor corresponding to the pixel value difference between the first and second intermediate images. More specifically, the weighting factor calculating unit 343 calculates a weighting factor $w(x, y)$ from a feature amount $TR(x, y)$ for each pixel based on an existing rule. The weighting factor calculating unit 343 calculates the weighting factor $w(x, y)$ by using, for example, the sigmoid function represented by equation (1) given below.

$$W(x,y)=1.0/(1.0+\exp(\text{Beta}*(\text{Alpha}-TR(x,y)))) \quad (1)$$

Alpha and Beta are parameters which can be set to arbitrary values via the input unit 38. For example, Alpha and Beta are set to 400 and 0.02, respectively.

The resultant image generating unit 344 generates a resultant image concerning the weighted addition of the first and second intermediate images based on the weighting factor. More specifically, the resultant image generating unit 344 executes weighted addition of an intermediate image ORG(x, y) and an intermediate image HALF(x, y) based on the weighting factor $w(x, y)$ according to equation (2) given below. For example, the resultant image generating unit 344 multiplies the intermediate image ORG(x, y) by a weight $(1-w(x, y))$, and multiplies the intermediate image HALF(x, y) by a weight $w(x, y)$. This weighted addition generates a resultant image RESULT1(x, y).

$$\text{RESULT1}(x,y)=(1-w(x,y))*\text{ORG}(x,y)+w(x,y)*\text{HALF}(x,y) \quad (2)$$

An example of the operation of the X-ray CT apparatus according to the first embodiment will be described next. The scanning scheme according to the first embodiment can be applied to both helical scanning and circular orbit scanning.

An example of the operation of the gantry 10 in helical scanning will be described first. In helical scanning, the control unit 31 controls the rotation driving unit 15 to repeatedly rotate the rotating frame 11. Continuously rotating the rotating frame 11 will continuously rotate the X-ray tube 12 and the X-ray detector 13 about the rotation axis Z. Concurrently with the rotation of the rotating frame 11, the control unit 31 controls the top driving unit 23 to move the top 21 along the body axis Z based on the moving amount of the top 21 per rotation of the rotating frame 11. During the rotation of the rotating frame 11, the control unit 31 controls the high voltage generating unit 14 to make the X-ray tube 12 repeatedly generate X-rays. The X-rays generated by the X-ray tube 12 are transmitted through the subject P and detected by the X-ray detection elements in the X-ray detector 13. The X-ray detection elements generate electrical signals corresponding to the intensities of the detected X-rays. The DAS 17 acquires projection data based on the electrical signals via the X-ray detection elements under the control of the control unit 31.

In this manner, helical scanning is executed by repeating the rotation of the rotating frame 11, the movement of the top 21, the generation of X-rays, and the acquisition of projection data.

An example of the operation of the gantry 10 in circular orbit scanning will be described next. In circular orbit scanning, the control unit 31 controls the rotation driving unit 15 to repeatedly rotate the rotating frame 11. Continuously rotating the rotating frame 11 will continuously rotate the X-ray tube 12 and the X-ray detector 13 about the rotation axis Z. During the rotation of the rotating frame 11, the control unit 31 stops the top 21. In addition, during the rotation of the rotating frame 11, the control unit 31 controls the high voltage generating unit 14 to make the X-ray tube 12 repeatedly generate X-rays. The X-rays generated by the X-ray tube 12 are transmitted through the subject P and detected by the X-ray detection elements in the X-ray detector 13. The X-ray detection elements generate electrical signals corresponding to the intensities of the detected X-rays. The DAS 17 acquires projection data based on the electrical signals via the X-ray detection elements under the control of the control unit 31.

In this manner, circular orbit scanning is repeatedly executed by the rotation of the rotating frame 11, the generation of X-rays, and the acquisition of projection data. Note that the scanning scheme of repeatedly performing circular orbit scanning is also called dynamic scanning. This embodiment can be applied to both single circular orbit scanning and multiple circular orbit scanning (dynamic scanning).

As described above, when helical scanning or circular orbit scanning is executed, the DAS 17 acquires projection data. The projection data storage unit 33 stores the acquired projection data via the I/F unit 32. The reconstruction unit 34 reads out projection data stored in the projection data storage unit 33, and reconstructs a resultant image (axial slice image) based on the readout projection data.

An example of the operation for resultant image generating processing according to the first embodiment, which is performed by the reconstruction unit 34, will be described below with reference to FIG. 3. Note that a reconstruction slice is set in advance automatically or via the input unit 38. For a concrete explanation, assume that the first intermediate image is the intermediate image ORG(x, y), and the second intermediate image is the intermediate image HALF(x, y).

First of all, the intermediate image generating unit 341 reads out the projection data acquired by the DAS 17 from the projection data storage unit 33. In step S301, the intermediate image generating unit 341 extracts a full projection data set, of the readout projection data, which can contribute to the image reconstruction of a reconstruction slice associated with the z position of the reconstruction target. In step S302, the intermediate image generating unit 341 generates a weighted full projection data set by applying weighting for data redundancy correction to the full projection data set, and generates the intermediate image ORG(x, y) from the weighted full projection data set by the filter+three-dimensional back projection method. In step S303, the intermediate image generating unit 341 extracts a half projection data set from the full projection data set extracted in step S302. In step S304, the intermediate image generating unit 341 generates the intermediate image HALF(x, y) by performing weighting for data redundancy correction and the filter+three-dimensional back projection method for the half projection data set as in step S302.

When the intermediate image ORG(x, y) and the intermediate image HALF(x, y) are generated, step S305 is performed. In step S305, the feature amount calculating unit 342 calculates a feature amount TR(x, y) based on the intermediate images ORG(x, y) and HALF(x, y).

In step S306, the weighting factor calculating unit 343 calculates the weighting factor w(x, y) by applying the feature amount TR(x, y) calculated in step S305 to equation (1). In step S307, the resultant image generating unit 344 executes the weighted addition represented by equation (2) for the intermediate image ORG(x, y) and the intermediate image HALF(x, y) by using the weighting factor w(x, y) calculated in step S306. This weighted addition generates a resultant image RESULT1(x, y) associated with a reconstruction slice.

When one resultant image RESULT1(x, y) is obtained, steps S301 to S307 are repeated for a reconstruction slice associated with another Z position. With this operation, the resultant image generating unit 344 obtains the resultant image RESULT1(x, y) associated with an arbitrary reconstruction slice included in the scan range.

The effects of the first embodiment will be described next.

As described above, the intermediate image generating unit 341 according to this embodiment generates the first intermediate image based on the first projection data set, and generates the second intermediate image based on the second projection data set. In this case, the first and second intermediate images are associated with the same reconstruction slice. The second projection data set is smaller in the number of views than the first projection data set. The second intermediate image is higher in time resolution than the first intermediate image. The resultant image generating unit 344 generates a resultant image associated with the weighted addition of the first and second intermediate images.

A weighting factor depends on a feature amount as indicated by equation (1). A feature amount depends on the pixel value difference between the first and second intermediate images. Therefore, the weighting factor changes in accordance with the degree of the movement of an imaging target. That is, the reconstruction unit 34 can automatically adjust the degree of contribution of the first intermediate image to a resultant image and the degree of contribution of the second intermediate image to the resultant image, i.e., the weighting factor w, in accordance with the degree of movement of the imaging target.

More specifically, consider a case in which the scanning scheme to be used is helical scanning, the beam pitch is set to 1 or less, which is relatively slow, for image noise reduction, and the number of views of projection data corresponds to one or more rotations. In this case, if the feature amount TR is large, the second intermediate image based on the second projection data set with a small number of views contributes more to a resultant image than the first intermediate image based on the first projection data set with a large number of views. This improves the time resolution of the resultant image. For example, the lung fields greatly moves accompanying the pulsation of the heart. Therefore, the resultant image associated with the lung fields which is generated by the first embodiment exhibits better time resolution than the prior art, and does not include much image noise. If the feature amount TR is small, the first intermediate image contributes more to a resultant image than the second intermediate image. This reduces the image noise of the resultant image. For example, the head portion does not move much during scanning. The image noise of the resultant image associated with the head portion which is generated by the first embodiment is reduced as compared with the prior art. In addition, since the first intermediate image requires more projection data than the second intermediate image, if the feature amount TR is small, it is possible to prevent degradation in data use efficiency.

The first embodiment can therefore provide an X-ray CT apparatus and image processing apparatus which can improve time resolution without increasing image noise.

In the above embodiment, the image processing apparatus 30 is mounted in the X-ray CT apparatus. However, the first embodiment is not limited to this. For example, the image processing apparatus 30 may be a workstation connected to the X-ray CT apparatus via a network.

Second Embodiment

A reconstruction unit 34 according to the second embodiment generates a resultant image based on a single first intermediate image and a plurality of second intermediate images.

An example of the operation for resultant image generating processing according to the second embodiment which is performed by the reconstruction unit 34 will be described below with reference to FIG. 4. Assume that a reconstruction slice is set in advance automatically or input via an input unit 38. In addition, the first and second projection data sets according to the second embodiment may satisfy the limitation defined by (A≥a)>(b≥B) described above. For a concrete explanation, assume that the first intermediate image based on the first projection data set is an intermediate image ORG based on a full projection rate set, and the second intermediate image based on the second projection data set is an intermediate image HALF based on a half projection data set. Furthermore, a scanning scheme according to the second embodiment can be applied to both circular orbit scanning (dynamic scanning) and helical scanning.

As shown in FIG. 4, in step S401, an intermediate image generating unit 341 extracts a full projection data set which can contribute to the image reconstruction of a reconstruction slice (a projection data set including all the views which can contribute to the image reconstruction of a reconstruction slice) from projection data. In step S402, the intermediate image generating unit 341 generates the intermediate image ORG based on the full projection data set. More specifically, in step S402, the intermediate image generating unit 341 generates an intermediate image ORG(x, y, z) by performing weighting for data redundancy correction and the filter+ three-dimensional back projection method for the full projection data set as in the first embodiment.

In step S403, the intermediate image generating unit 341 extracts a plurality of half projection data sets (projection data corresponding to 180°+fan angle) from the full projection data set extracted in step S401. The respective half projection data sets differ in view center, i.e., the acquisition time of projection data. That is, the respective half projection data sets are associated with a plurality of acquisition times. The plurality of half projection data sets include a common reconstruction slice z. In step S404, more specifically, the intermediate image generating unit 341 extracts n half projection data sets from the full projection data sets while changing the view central position. In step S404, the intermediate image generating unit 341 generates n intermediate images HALF based on the n half projection data sets. More specifically, in step S4041, the intermediate image generating unit 341 generates an intermediate image HALF(x, y, z, 1) by performing weighting for data redundancy correction and the filter+ three-dimensional back projection method like those in the first embodiment for the first half projection data set. Likewise, in step S4042, the intermediate image generating unit 341 generates an intermediate image HALF(x, y, z, 2) based on the second half projection data set. In this manner, the intermediate image generating unit 341 generates the intermediate image HALF for each of all the n half projection data sets. The n intermediate images HALF respectively have different view centers, and hence can be said to belong to the different acquisition times.

In step S405, a feature amount calculating unit 342 generates a time-resolution-priority intermediate image TR(x, y, z) based on n intermediate images HALF(x, y, z, 1), . . . , (x, y, z, n). In this manner, the feature amount calculating unit 342 functions as a time-resolution-priority intermediate image TR generating unit. More specifically, the feature amount calculating unit 342 calculates the intermediate image TR(x, y, z) with optimal time resolution from the n intermediate images HALF. If the difference between an image at time t and an image at time t+1 is minimum, the image at time t or the image at time t+1 indicates the small movement of the imaging target with the lapse of time. That is, this indicates that the time resolution is optimal. More specifically, the intermediate image TR(x, y, z) is calculated according to equation (3).

$$TR[x, y, z] = \operatorname*{argmin}_{t}\left(\sum_{x,y} |HALF[x, y, z, t+1] - HALF[x, y, z, t]|\right) \quad (3)$$

That is, the feature amount calculating unit 342 calculates the absolute value of the difference between the luminance value of each of a plurality of pixels and that of a corresponding pixel for the images at two temporally consecutive acquisition times t and t+1, and calculates the total sum of the absolute values of the calculated differences. The feature amount calculating unit 342 then calculates the total sum of the absolute values of the differences between all the acquisition time pairs. The feature amount calculating unit 342 then specifies an image at the time when the total sum of the absolute values of differences becomes minimum. The specified image is handled as the intermediate image TR(x, y, z). In this manner, the feature amount calculating unit 342 specifies, as the time-resolution-priority intermediate image TR, the image HALF exhibiting a minimum pixel value change from the plurality of intermediate images HALF.

Note that the method of calculating the intermediate image TR is not limited to the above method. For example, it is possible to use, as a pixel value change, the total sum of correction coefficients obtained by pattern matching or the total sum of the vector lengths of optical flows instead of the total sum of the absolute values of the differences between luminance values.

There is no need to consider the total sum of the values of all the pixels constituting one image, and a pixel value may be calculated for each pixel. For example, the pixel value of an image at time $t_a$ may be used for a pixel A, and the pixel value of an image at time $t_B$ may be used for a pixel B. In this manner, the feature amount calculating unit 342 may specify a pixel exhibiting the minimum pixel value change for each of a plurality of pixels constituting the plurality of intermediate images HALF and generate the intermediate image TR based on the specified pixels.

If the CT value of an imaging target is known in advance, the feature amount calculating unit 342 may additionally performs processing such as discriminating noise by performing filtering using the CT value.

In step S406, a weighting factor calculating unit 343 calculates an intermediate image ORG(x, y, z), an intermediate image TR (x, y, z), and a weighting factor w(x, y, z) for each pixel. The weighting factor is calculated according to, for example, equation (1) described above.

In step S407, a resultant image generating unit 344 generates a resultant image associated with weighted addition of the intermediate image ORG and the time-resolution-priority intermediate image TR based on the weighting factor. More specifically, the resultant image generating unit 344 executes weighted addition of an intermediate image ORG(x, y, z) and the intermediate image TR(x, y, z) based on the weighting factor w(x, y, z) according to equation (4) given below. For example, the resultant image generating unit 344 multiplies the intermediate image ORG(x, y, z) by a weight (1−w(x, y, z)), and multiplies the intermediate image TR(x, y, z) by a weight w(x, y, z). This weighted addition generates a resultant image RESULT2(x, y, z).

$$RESULT2(x,y,z)=(1-w(x,y,z))*ORG(x,y,z)+w(x,y,z)*TR(x,y,z) \quad (4)$$

Upon obtaining one resultant image RESULT2(x, y, z), this apparatus repeats steps S401 to S407 for a reconstruction slice associated with another Z position. This obtains the resultant image RESULT2(x, y, z) associated with an arbitrary reconstruction slice included in the scan range.

The reconstruction unit 34 according to the second embodiment described above generates a resultant image based on the single first intermediate image and the plurality of second intermediate images. In this case, the reconstruction unit 34 generates a time-resolution-priority intermediate image based on the plurality of second intermediate images, and generates a resultant image based on the first intermediate image and the time-resolution-priority intermediate image.

As described above, a time-resolution-priority intermediate image is an image, of the plurality of second intermediate images, which is formed by a pixel region exhibiting the smallest movement with the lapse of time. In other words, a time-resolution-priority intermediate image is an image formed by a pixel region, of the plurality of second intermediate images, which has the optimal time resolution. That is, a time-resolution-priority intermediate image is typically an image having better time resolution than the second intermediate image.

The reconstruction unit 34 according to the second embodiment can automatically adjust the degree of contribution of the first intermediate image to the resultant image and the degree of contribution of the time-resolution-priority intermediate image to the resultant image, i.e., the weighting factor w, in accordance with the degree of movement of the imaging target.

If the movement of an imaging target is large, the time-resolution-priority intermediate image contributes more to the resultant image than the first intermediate image. This improves the time resolution of the resultant image as compared with the first embodiment. If the movement of an imaging target is small, the first intermediate image contributes more to the resultant image than the time-resolution-priority intermediate image. This reduces the image noise of the resultant image. The time-resolution-priority intermediate image requires more projection data than the second intermediate image, and the data use efficiency in the second embodiment is improved as compared with the first embodiment.

The second embodiment can therefore provide an X-ray CT apparatus and image processing apparatus which can improve time resolution without degrading image noise.

In the above embodiment, the image processing apparatus is mounted in the X-ray CT apparatus. However, the second embodiment is not limited to this. For example, the image processing apparatus may be a workstation connected to the X-ray CT apparatus via a network.

If the movement of an imaging target is relatively small, the average image of a plurality of second intermediate images may be handled as a time-resolution-priority intermediate image. An average image is generated by using more projection data than that required for the above time-resolution-priority intermediate image. This achieves improvements in the image noise of the resultant image and data use efficiency.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
   an X-ray tube configured to generate X-rays;
   an X-ray detector configured to detect X-rays which are generated by the X-ray tube and transmitted through a subject;
   a support mechanism configured to rotatably support the X-ray tube and the X-ray detector;
   a control unit configured to control the support mechanism to rotate the X-ray tube and the X-ray detector;
   an acquisition unit configured to acquire projection data associated with the subject via the X-ray detector;
   an intermediate image generating unit configured to extract a full projection data set from the acquisition unit which contributes to image reconstruction of a reconstruction slice, generate a first intermediate image using the data in the full projection data set, the full projection data set having a first view angle range, and generate a second intermediate image based on a second projection data set, the second projection data set being less than an entire portion of the full projection data set and having a second view angle range narrower than the first view angle range;
   a weighting factor calculating unit configured to calculate a weighting factor corresponding to a pixel value difference between the first intermediate image and the second intermediate image; and
   a resultant image generating unit configured to generate a resultant image associated with weighted addition of the first intermediate image and the second intermediate image based on the weighting factor.

2. The apparatus according to claim 1, wherein the number of views included in the first view angle range is set to be not more than the number of views which are configured to contribute to image reconstruction at a reconstruction slice position and to be larger than the number of views included in 180°+fan angle, and
   the number of views included in the second view angle range is set to be less than the number of views which are configured to contribute to image reconstruction at the reconstruction slice position and to be not less than the number of views included in 180°+fan angle.

3. The apparatus according to claim 2, wherein the number of views which are configured to contribute to image reconstruction at the reconstruction slice position is decided in accordance with one of a scan condition and a reconstruction condition.

4. The apparatus according to claim 1, which further comprises a pixel value difference calculating unit configured to calculate the pixel value difference between the first intermediate image and the second intermediate image for each pixel, and in which
   the weighting factor calculating unit calculates the weighting factor for each pixel based on the calculated pixel value difference.

5. The apparatus according to claim 1, wherein the control unit controls the support mechanism to repeatedly rotate the X-ray tube and the X-ray detector.

6. The apparatus according to claim 1, which further comprises a bed configured to support a top so as to allow the top to move along a rotation axis of the X-ray tube and the X-ray detector, and in which
   the control unit controls the support mechanism to repeatedly rotate the X-ray tube and the X-ray detector and controls the bed to move the top along the rotation axis.

7. The apparatus according to claim 1, wherein the pixel value difference is calculated based on one of a difference between the first intermediate image and the second intermediate image, a correlation coefficient associated with the first intermediate image and the second intermediate image, and an optical flow associated with the first intermediate image and the second intermediate image.

8. An X-ray computed tomography apparatus comprising:
   an X-ray tube configured to generate X-rays;
   an X-ray detector configured to detect X-rays which are generated by the X-ray tube and transmitted through a subject;
   a support mechanism configured to rotatably support the X-ray tube and the X-ray detector;
   a control unit configured to control the support mechanism to repeatedly rotate the X-ray tube and the X-ray detector;
   an acquisition unit configured to acquire projection data associated with the subject via the X-ray detector;
   an intermediate image generating unit configured to generate a first intermediate image based on a first projection data set of the projection data and generate a plurality of second intermediate images based on a plurality of second projection data sets of the projection data respectively, the second projection data sets being associated with a plurality of scan times respectively, the first projection data set including the number of views larger than the number of views included in the second projection data set;

a third intermediate image generating unit configured to generate a third intermediate image of a time-resolution-priority type based on the second intermediate images;

a weighting factor calculating unit configured to calculate a weighting factor corresponding to a pixel value difference between the first intermediate image and the third intermediate image; and a resultant image generating unit configured to generate a resultant image associated with weighted addition of the first intermediate image and the third intermediate image based on the weighting factor.

9. The apparatus according to claim 8, wherein the third intermediate image generating unit specifies, as the third intermediate image, an image of the second intermediate images, a specified image exhibiting a smallest pixel value change.

10. The apparatus according to claim 9, wherein a pixel value change is calculated based on one of a difference between the second intermediate images, a correlation coefficient associated with the second intermediate images, and an optical flow associated with the second intermediate images.

11. The apparatus according to claim 8, wherein the third intermediate image generating unit specifies a pixel, of plurality of pixels constituting the second intermediate images, the specified pixel exhibiting a minimum pixel value change, and generates the third intermediate image based on the specified pixel.

12. The apparatus according to claim 11, wherein a pixel value change is calculated based on one of a difference between the second intermediate images, a correlation coefficient associated with the second intermediate images, and an optical flow associated with the second intermediate images.

13. The apparatus according to claim 8, wherein a number of views included in the first view angle range is set to be not more than a number of views which are configured to contribute to image reconstruction at a reconstruction slice position and to be larger than a number of views included in 180°+fan angle, and a number of views included in the second view angle range is set to be less than the number of views which are configured to contribute to image reconstruction at the reconstruction slice position and to be not less than the number of views included in 180°+fan angle.

14. The apparatus according to claim 8, wherein the control unit controls the support mechanism to repeatedly rotate the X-ray tube and the X-ray detector.

15. The apparatus according to claim 8, which further comprises a bed configured to support a top so as to allow the top to move along a rotation axis of the X-ray tube and the X-ray detector, and in which the control unit controls the support mechanism to repeatedly rotate the X-ray tube and the X-ray detector and controls the bed to move the top along the rotation axis.

16. An image processing apparatus comprising:

a storage unit configured to store projection data associated with a subject;

an intermediate image generating unit configured to extract a full projection data set from the storage unit which contributes to image reconstruction of a reconstruction slice, generate a first intermediate image using the data in the full projection data set, the full projection data set having a first view angle range, and generate a second intermediate image based on a second projection data set, the second projection data set being less than an entire portion of the full projection data set and having a second view angle range narrower than the first view angle range;

a weighting factor calculating unit configured to calculate a weighting factor corresponding to a pixel value difference between the first intermediate image and the second intermediate image; and a resultant image generating unit configured to generate a resultant image associated with weighted addition of the first intermediate image and the second intermediate image based on the weighting factor.

17. An image processing apparatus comprising:

a storage unit configured to store projection data acquired by helical scanning or circular orbit scanning performed a plurality of number of times;

an intermediate image generating unit configured to generate a first intermediate image based on a first projection data set of the projection data and generate a plurality of second intermediate images based on a plurality of second projection data sets of the projection data respectively, the second projection data sets being associated with a plurality of scan times respectively, the first projection data set including the number of views larger than the number of views included in the second projection data sets;

a third intermediate image generating unit configured to generate a single third intermediate image of a time-resolution-priority type based on the second intermediate images;

a weighting factor calculating unit configured to calculate a weighting factor corresponding to a pixel value difference between the first intermediate image and the third intermediate image; and a resultant image generating unit configured to generate a resultant image associated with weighted addition of the first intermediate image and the third intermediate image based on the weighting factor.

18. The apparatus according to claim 1, wherein the second projection data set comprises a half projection data set.

19. The apparatus according to claim 1, wherein the intermediate image generating unit is configured to generate the first intermediate image using all of the data in the full projection data set.

20. The apparatus according to claim 16, wherein the second projection data set comprises a half projection data set.

21. The apparatus according to claim 16, wherein the intermediate image generating unit is configured to generate the first intermediate image using all of the data in the full projection data set.

* * * * *